(12) United States Patent
Ho et al.

(10) Patent No.: US 11,712,153 B2
(45) Date of Patent: Aug. 1, 2023

(54) ENDOSCOPE HAVING AN ADDITIONAL EXTERNAL WORKING CHANNEL

(71) Applicant: Ovesco Endoscopy AG, Tübingen (DE)

(72) Inventors: Chi-Nghia Ho, Reutlingen (DE); Alexander Meining, Ulm (DE)

(73) Assignee: Ovesco Endoscopy AG

( * ) Notice: Subject to any disclaimer, the term of this patent is extended or adjusted under 35 U.S.C. 154(b) by 206 days.

(21) Appl. No.: 16/603,392

(22) PCT Filed: Apr. 6, 2018

(86) PCT No.: PCT/EP2018/058874
§ 371 (c)(1),
(2) Date: Oct. 7, 2019

(87) PCT Pub. No.: WO2018/185293
PCT Pub. Date: Oct. 11, 2018

(65) Prior Publication Data
US 2020/0046201 A1 Feb. 13, 2020

(30) Foreign Application Priority Data

Apr. 7, 2017 (DE) .................. 102017107546.1

(51) Int. Cl.
*A61B 1/00* (2006.01)
*A61B 1/005* (2006.01)
*A61B 17/00* (2006.01)

(52) U.S. Cl.
CPC ........ *A61B 1/0014* (2013.01); *A61B 1/00087* (2013.01); *A61B 1/00128* (2013.01);
(Continued)

(58) Field of Classification Search
CPC ............ A61B 1/00087; A61B 1/00119; A61B 1/00121; A61B 1/0014
See application file for complete search history.

(56) References Cited

U.S. PATENT DOCUMENTS 6,022,313 A * 2/2000 Ginn .................... A61B 1/0014
600/104
6,071,233 A * 6/2000 Ishikawa .............. A61B 1/0014
600/104
(Continued)

FOREIGN PATENT DOCUMENTS

DE 102007008099 A1 8/2008
DE 102009014178 A1 9/2010
(Continued)

OTHER PUBLICATIONS

German Search Report for German Application No. 10 2017 107 546.1, with English translation, dated Dec. 7, 2017, 18 pages.
(Continued)

*Primary Examiner* — Matthew J Kasztejna
(74) *Attorney, Agent, or Firm* — RatnerPrestia (57) ABSTRACT

A working channel device is mountable on the outer circumference of an endoscope, such as an endoscope of the flexible shaft design. The device has a tubular or hose-like working channel and a distal fixing element that can be fixed to the working channel. The distal fixing element can engage around the endoscope in a clamping manner at the endoscope head of the endoscope. A proximal fixing element can be fixed to the working channel, which can engage around the endoscope, preferably at the endoscope grip of the endoscope. A preferably sleeve-like adapter can be mounted at the proximal end of the working channel of the working channel device. The adapter has or forms the proximal fixing element and additionally forms a connection point/interface for the connection of medical devices.

25 Claims, 8 Drawing Sheets

(52) U.S. Cl.
CPC .......... *A61B 1/00135* (2013.01); *A61B 1/005* (2013.01); *A61B 2017/00296* (2013.01)

(56) References Cited

U.S. PATENT DOCUMENTS

| | | | | |
|---|---|---|---|---|
| 6,309,346 | B1 * | 10/2001 | Farhadi | A61B 1/00156 600/114 |
| 6,878,106 | B1 * | 4/2005 | Herrmann | A61B 1/00073 600/104 |
| 6,997,931 | B2 * | 2/2006 | Sauer | A61B 1/0014 600/104 |
| 7,179,223 | B2 * | 2/2007 | Motoki | A61B 1/00039 600/102 |
| 7,198,599 | B2 * | 4/2007 | Goto | A61B 1/0125 600/154 |
| 7,566,300 | B2 * | 7/2009 | Devierre | A61B 1/00087 600/104 |
| 7,575,548 | B2 * | 8/2009 | Takemoto | A61B 1/00087 600/104 |
| 7,588,580 | B2 * | 9/2009 | Okada | A61B 1/00087 600/104 |
| 7,922,650 | B2 * | 4/2011 | McWeeney | A61M 25/0068 600/104 |
| 8,157,798 | B2 * | 4/2012 | Takahashi | A61B 18/14 606/47 |
| 8,353,815 | B2 * | 1/2013 | Okada | A61B 1/012 600/104 |
| 8,535,220 | B2 * | 9/2013 | Mondschein | A61B 1/00091 600/157 |
| 8,727,967 | B2 * | 5/2014 | Weitzner | A61B 1/00154 600/106 |
| 8,906,014 | B2 | 12/2014 | Bacher et al. | |
| 9,486,125 | B2 * | 11/2016 | James | A61B 1/0014 |
| 9,931,019 | B2 | 4/2018 | Herrmann et al. | |
| 10,136,798 | B2 | 11/2018 | Yamaya | |
| 2004/0210111 | A1 | 10/2004 | Okada | |
| 2005/0065399 | A1 * | 3/2005 | Sasaki | A61B 1/018 600/106 |
| 2005/0234297 | A1 | 10/2005 | Devierre et al. | |
| 2006/0235457 | A1 * | 10/2006 | Belson | A61B 1/018 606/191 |
| 2008/0277853 | A1 | 11/2008 | Menn | |
| 2010/0036198 | A1 * | 2/2010 | Tacchino | A61B 17/29 600/106 |
| 2013/0310641 | A1 | 11/2013 | Terliuc et al. | |
| 2016/0206178 | A1 * | 7/2016 | Lau | A61M 25/01 |

FOREIGN PATENT DOCUMENTS

| | | |
|---|---|---|
| EP | 1284120 A1 | 2/2003 |
| JP | 07155283 A | 6/1995 |
| JP | 2003210399 A | 7/2003 |
| JP | 2004230139 A | 8/2004 |
| JP | 2005131107 A | 5/2005 |
| JP | 2005131211 A | 5/2005 |
| WO | 2005039427 A1 | 5/2005 |
| WO | 2008098124 A1 | 8/2008 |
| WO | 2016092981 A1 | 6/2016 |

OTHER PUBLICATIONS

International Search Report and Written Opinion for International Application PCT/EP2018/058874, dated Jul. 2, 2018, 10 pages.
Japanese Notice of Reasons for Refusal for Japanese Application No. 2019-554864, dated Feb. 18, 2022, with translation, 24 pages.
European Communication for European Application No. 18 719 763.7, dated May 31, 2023 with translation, 9 pages.

* cited by examiner

ENDOSCOPE HAVING AN ADDITIONAL EXTERNAL WORKING CHANNEL

CROSS-REFERENCE TO RELATED APPLICATIONS

This application is the United States national phase entry of International Application No. PCT/EP2018/058874, filed Apr. 6, 2018, which claims the benefit of priority of German Application No. 10 2017 107 546.1, filed Apr. 7, 2017. The contents of International Application No. PCT/EP2018/058874 and German Application No. 10 2017 107 546.1 are incorporated by reference herein in their entireties.

FIELD

The invention relates to an adaptive, external/separate working channel device for optional mounting on the outer circumference of an endoscope, in particular of the flexible shaft design, and an endoscope of the (flexible) shaft design with such an external working channel (Additional Working Channel, AWC for short). The AWC is prepared to be mounted on/around an endoscope/endoscope head and to be aligned to it in any desired or predefined position.

SUMMARY

The AWC according to the invention essentially has four components.

- A first component is realized by a distal end cap or clamp/spring clip, which (regarding its inner diameter) is designed to establish a plug/snap-on or clip connection with the distal end (endoscope head) of the (common/conventional) endoscope. Apart from the snap-on connection, the end cap or clamp/spring clip can preferably additionally be fixed with an adhesive tape, which is selectively either firmly connected to the end cap or clamp/spring clip or is enclosed as a separate additional component.
- A second component is realized by a hose or a flexible pipe sleeve, which forms the additional working channel and which can be connected to or is fixedly connected to the end cap or clamp/spring clip. The hose/pipe sleeve is preferably cut at the distal end, or is or can be cut to length according to the current axial length of the endoscope shaft. In addition, further attachment positions/mounting means, e.g. for additional adhesive strips or clips or Velcro tapes, may be present/provided at the hose/pipe sleeve, preferably at even distances, by means of which the hose can be fixed to the endoscope shaft between the endoscope head and its endoscope grip provided as standard.
- A third component relates to a releasable fixing means for the temporary/optional mounting of the proximal end portion of the separate hose/pipe sleeve on the endoscope grip, for example consisting of two clip-type or wing-type mounting lugs which can be mounted on the proximal end portion of the hose/pipe sleeve (after having been correctly cut to length) and have fastenings (eyelets/through holes/hooks/buttons and the like) at their free ends to which preferably a tension strap such as Velcro tape/rubber strap/belt, etc. can be fastened.
- A fourth component is realized by an adapter, which has an interface for standardized connection systems. This adapter is initially prepared to be attached in a sleeve-like manner to the proximal end of the hose/pipe sleeve, whereby the adapter also simultaneously carries the two clamp-like or wing-like mounting lugs, preferably integrally. Thus, conventional connection systems can also be coupled with the adapter in order to economically couple the AWC with other medical devices such as syringes/pumps, etc.

In other words, the invention relates to a retrofit kit for equipping an endoscope with an additional working channel (AWC). The set includes said additional working channel, which is formed as a flexible hose and is arranged and attached circumferentially at the shaft of the retrofitted endoscope; a distal fixing means, which is configured to connect the distal end of the additional working channel to the distal end of a retrofitted endoscope; a proximal fixing means, which is configured to fix the proximal end of the additional working channel to the handle portion of a retrofitted endoscope; and an adapter as an interface for medical instruments or devices, e.g. syringes.

According to one aspect of the invention, a cover hose may be provided as an additional (fifth) component which is adapted and configured to be pulled over the working channel and the endoscope adapted/retrofitted with it. The cover hose thus envelops the endoscope and the additional working channel arranged on it and can thus prevent tissue from being trapped between these two components, which can lead to complications (e.g. tearing of tissue and perforation).

According to a preferred configuration of the invention, the distal fixing means can form at least one endoscope-head stop, which fixes the distal fixing means with respect to the endoscope head by a form closure in its axial direction. This endoscope-head stop can preferably be configured in such a way that it contacts a front side/front surface of the endoscope head of an endoscope adapted with the working channel device. In this way, a form-fit is created that reliably prevents the additional working channel from slipping proximally when an endoscope retrofitted with the AWC is inserted.

According to a further preferred configuration, the distal fixing means may have a first accommodation with at least partial circular cross-section for accommodation of the working channel and a second accommodation adjacent to the first accommodation, aligned in parallel, with at least partial circular cross-section for accommodation of the endoscope head.

According to a preferred configuration of the invention, the first accommodation may have a sleeve shape open or slotted towards the second accommodation and the second accommodation may be formed by two crescent-shaped clamping arms extending away from the first accommodation. The distal end of the additional working channel can be correspondingly pushed into the sleeve-shaped first accommodation, while the crescent-shaped clamping arms with their inner surfaces form the second accommodation, which can clamp around a distal tip of a retrofitted endoscope. Due to its slotted sleeve shape, the first accommodation can serve by means of its inherent elasticity as a spring element to provide (at least part of) the clamping force of the clamping arms.

According to a further development of the above configuration, the crescent-shaped clamping arms of the distal fixing means can with their outer surfaces define a circular shape in a plane of a front surface of an adapted endoscope and the outer surface of the sleeve defining the first accommodation can project/protrude in the radial direction by no more than half the diameter of the first accommodation over this circular shape. In other words, the additional working channel can fit into the frontal silhouette of the distal fixing means. In contrast to conventional AWCs, in which the distal working channel end protrudes radially with its entire diameter from the outer circumference of the distal cap, the described constructive design results in better gliding properties when inserting a retrofitted endoscope.

According to a preferred configuration, the proximal fixing means can be integrally formed with the adapter. The adapter accordingly has two clamp-like, bow-like, or wing-like mounting lugs or cantilevers (preferably made of one piece of material), which serve to attach the adapter ergonomically to the grip of the endoscope. The cantilevers have holes in a first configuration and the adapter has a hook or button, all of which serve to engage a Velcro tape connection or other (tensioning) strap. In a second, alternative configuration, the cantilevers have hooks (hook-shaped extensions or buckles), which serve to snap or insert the endoscope grip into the hook-shaped extensions or buckles and additionally enable an additional elastic element/strap/tape/rubber to be hooked in, in order to be able to firmly clamp the handle.

According to a preferred configuration of the invention, the clamp-like, bow-like or wing-like mounting lugs or cantilevers can form at their free ends hooks facing away from each other, which can be tensioned against each other with a rubber ring or band to secure the mounting lugs or cantilevers enclosing the endoscope grip. Preferably, at least one of the mounting lugs or one of the cantilevers may have a retaining slit at its edge area adjacent to the hook at its free end. This retaining slit is open towards the edge of the mounting lug or cantilever, wherein this opening forms a narrow point (bottleneck). The rubber ring or rubber band is snapped (can be pre-mounted therein) through said narrow point and is thus held in the retaining slit. This prevents the rubber ring or rubber band from slipping out of the hooks and falling to the ground (becoming unsterile) when mounting the AWC to the endoscope grip.

According to a further aspect, the adapter may have an integrated valve or a valve may be mounted on the adapter which is intended to seal the working channel when an instrument is used in the working channel and/or to seal in such a way that no air/liquid can escape/flow from the patient's body.

BRIEF DESCRIPTION OF THE DRAWING FIGURES

The invention is explained in more detail in the following with reference to the accompanying figures using preferred exemplary embodiments. The figures are merely schematic in nature and serve exclusively to understand the invention. The same elements are provided with the same reference signs. They show.

DETAILED DESCRIPTION

Basically, the invention relates to a working channel device 1 for retrofitting a (commercially available) endoscope 2 of the flexible shaft design with an additional working channel 3, a so-called AWC (Additional Working Channel). Such endoscopes 2 are well known in the state of the art and are therefore only described very briefly in the following. An endoscope 2 of this type usually has an endoscope head 21 in which various functional units 25, which are not explained in more detail below, are arranged, such as an outlet of a primary (endoscope-internal) working channel, an optics for imaging and/or a lamp. Furthermore, such an endoscope 2 usually has a flexible shaft 22 with passively flexurally rigid portions and preferably an actively bendable portion (deflecting) as well as a grip 23 with various operating elements and terminals for connecting the various functional units 25 to a base station or the like.

The additional working channel 3 of the working channel device 1 according to the invention is formed by a hose 3 (or a tubular sleeve 3), which is applied during use to the endoscope shaft 22 and extends along and outside of it from the grip 23 to the endoscope head 21, so that (minimally invasive) tools and/or media can be introduced into a patient from the user side through the additional external working channel formed in this way.

Figure 9:
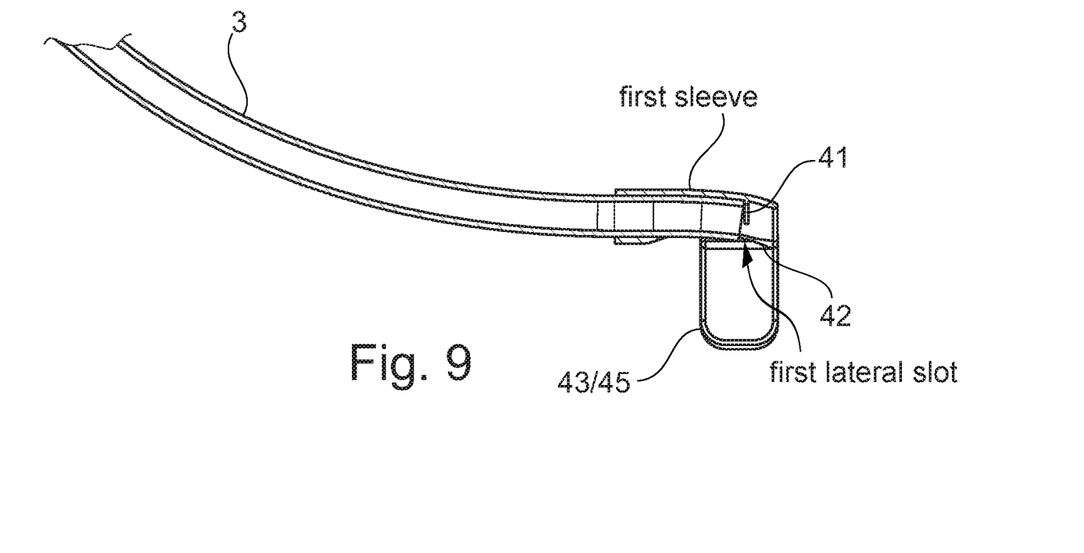
FIG. 9 shows a sectional view of the distal end cap in the preferred configuration.
Figure 10:
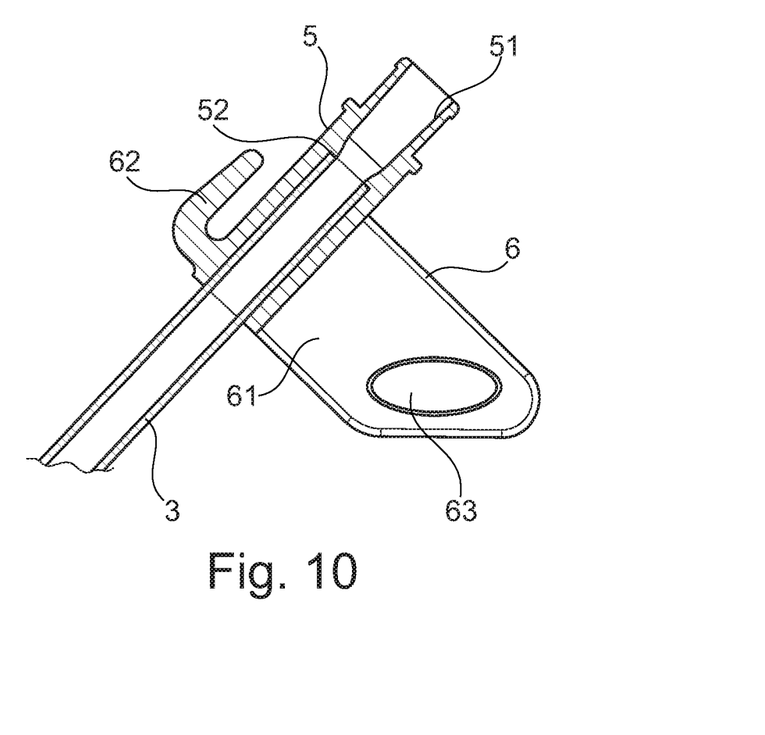
FIG. 10 shows a sectional view of the proximal fixing means of the working channel device according to the first configuration.

For a preferred exemplary embodiment, the working channel/hose 3 is first cut to length/cut off and adapted to the length of the endoscope shaft 22. To determine the alignment and axial position of the distal outlet of the working channel/hose 3, a distal fixing means (distal cap) 4 is provided at the distal end of the working channel/hose 3. This fixing means 4 encloses the outer circumference of the endoscope head 21 in a partial circle, preferably around about ⅘ of the outer circumference of the endoscope head, with an integrally formed fixing portion 43, which forms two crescent-shaped clamping arms 45 and can thus be fixed/ clipped to it in a clamping manner (see FIG. 3). As the sectional view (FIG. 9) of the distal fixing means 4 shows, it is pushed onto the working channel/hose 3 in a sleeve-like manner and is defined in relation to it via a stop 41. Preferably, the working channel/hose 3 generates by means of its inherent elasticity a clamping effect with the sleeve-like accommodation of the distal fixing means 4. The sleeve-like accommodation for the working channel/hose 3 is slotted on its side facing the fixing portion 43 and thus also serves as a spring element which, due to its inherent elasticity, enables a deflection of the crescent-shaped clamping arms 45 by overcoming a defined pre-stressing force. The partial circle-shaped fixing portion 43 also forms a stop 42, which preferably runs around the partial-circle shape of the fixing portion 43 and is complementary to the distal end circumferential edge of the endoscope head 21 in order to axially define the distal fixing means 4 with respect to the endoscope head 21. The fixing portion 43 of the distal fixing means 4 mainly interacts with the endoscope head 21 on its circumferential outer surface in order to leave the functional units lying in the front surface of the endoscope head 21 exposed or unobstructed. Preferably, the distal fixing means 4 can be additionally secured with a tape 44 against unintentional loosening due to excessive force.

Figure 1:
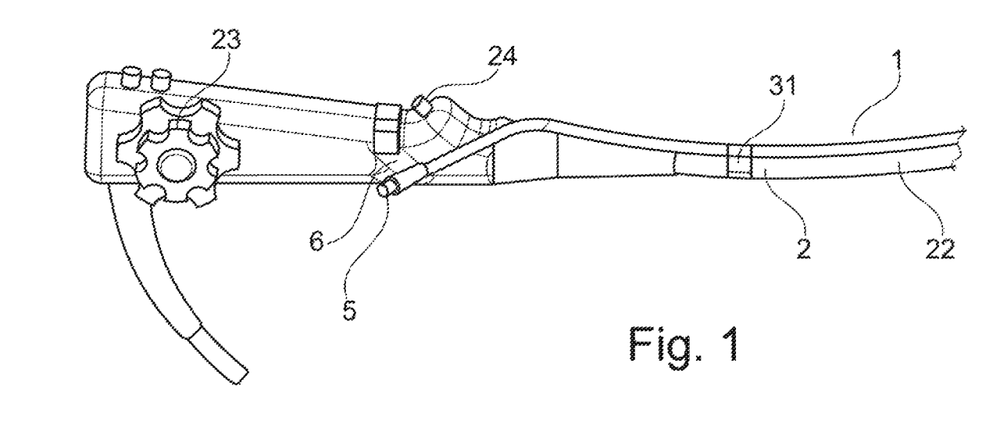
FIG. 1 shows an endoscope comprising an endoscope grip, an endoscope shaft as well as a working channel device according to a first configuration of the present invention.
Figure 2:
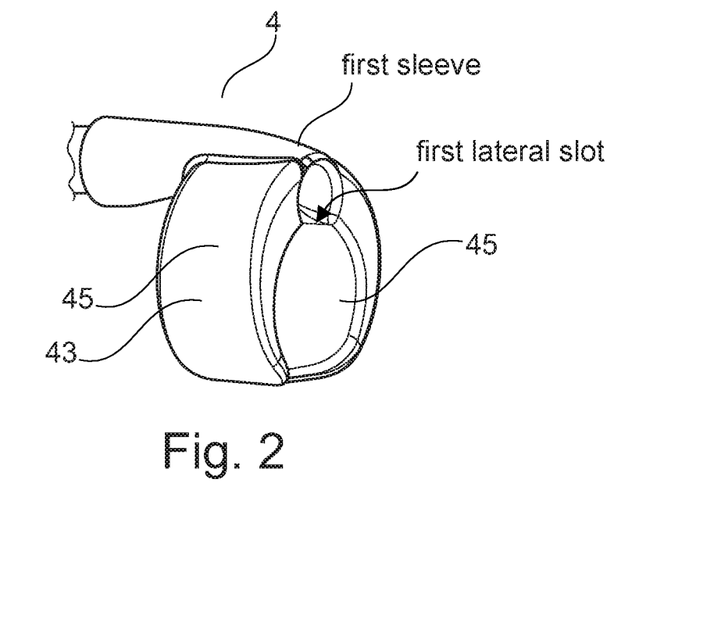
FIG. 2 shows a distal fixing means or a distal end cap of a working channel device according to the invention according to the first configuration.
Figure 3:
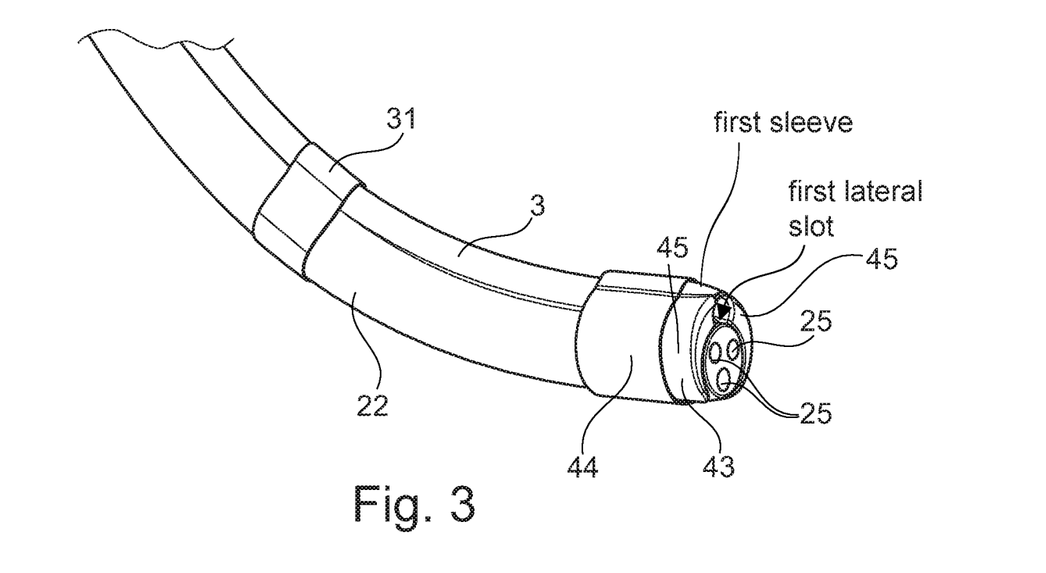
FIG. 3 shows a tube-shaped or hose-shaped working channel with the distal end cap according to the first configuration in a state mounted on an endoscope.
Figure 4:
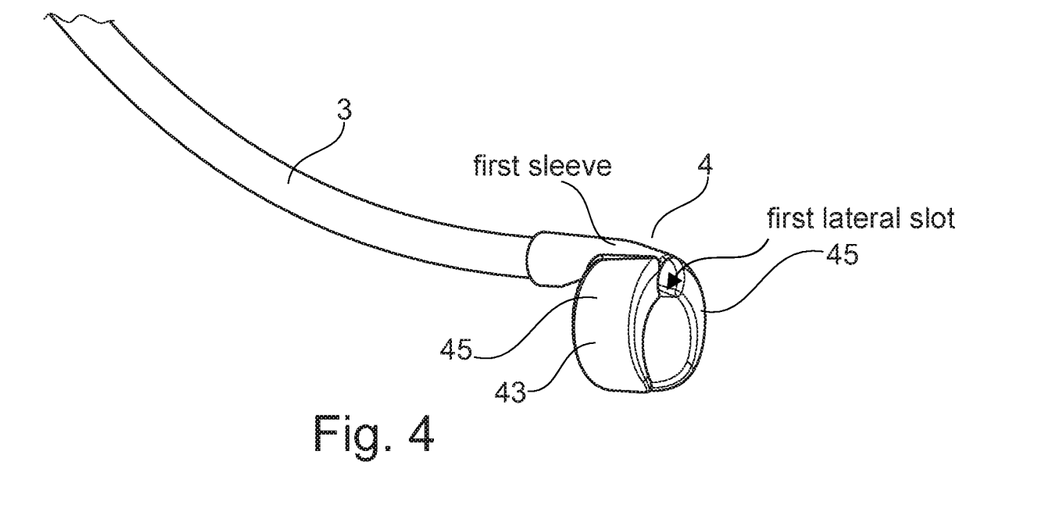
FIG. 4 shows the tube-shaped or hose-shaped working channel with the distal end cap according to the first configuration without endoscope.
Figure 5:
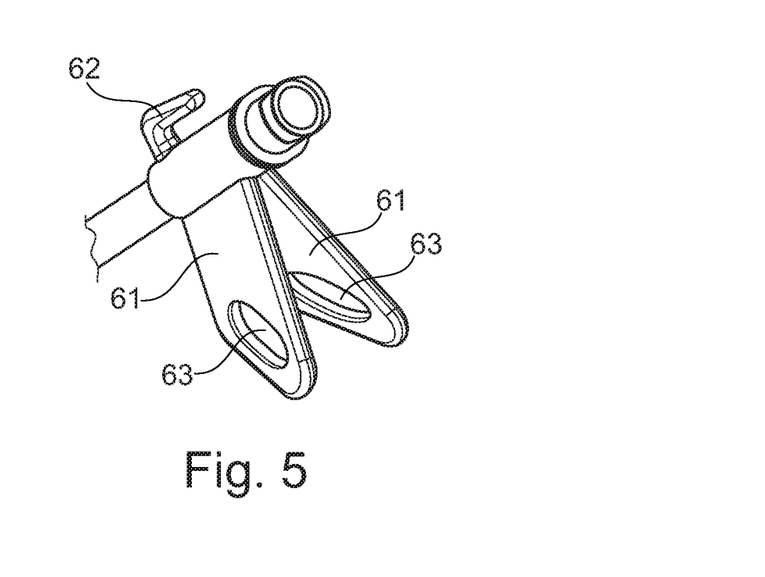
FIG. 5 shows a proximal fixing means of the working channel device according to the first configuration.
Figure 6:
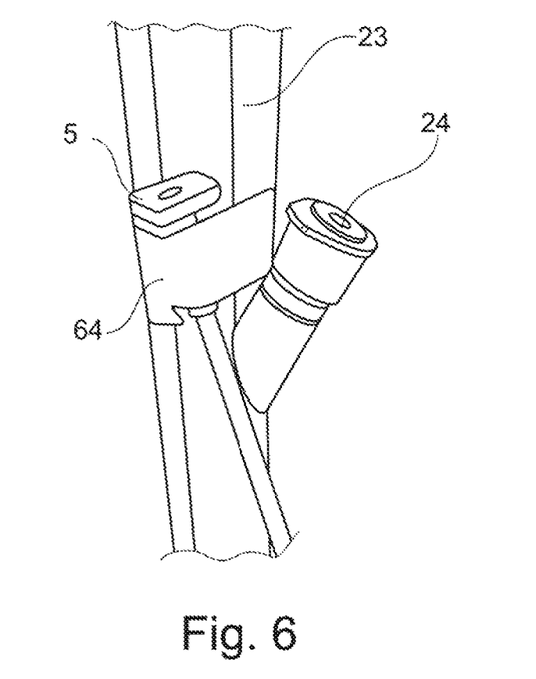
FIG. 6 shows the proximal fixing means of the working channel device according to the first configuration in a state when it is fixed to an endoscope grip.
Figures 7, 8:
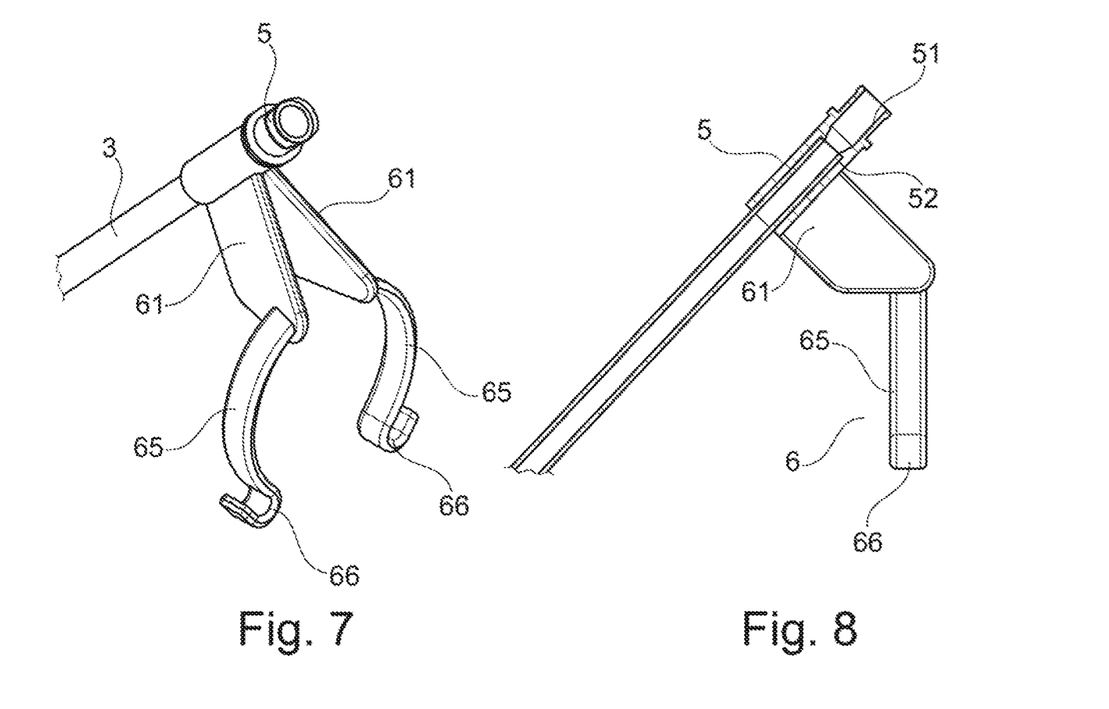
FIG. 7 shows a proximal fixing means of a working channel device according to a second configuration.
FIG. 8 shows a sectional view of the proximal fixing means of the working channel device according to the second configuration.

The fixing portion 43 or its clamping arms 45 are positioned in FIG. 3 in an upper area facing away from the adapted endoscope 2, so that the sleeve-shaped accommodation for the hose 3 does not protrude far beyond the clamping arms 45 in the radial direction. This results in a comparatively smooth/streamlined outer contour of the frontal silhouette of the distal fixing means 4, especially in combination with a rounded design of the distal circumferential edges of the distal cap 4.

In order to ensure that the working channel/hose 3 is in contact with the endoscope shaft 22, the working channel/hose 3 is fixed to it with tapes/adhesive tapes 31 or clips (not shown), preferably with even spacing.

A preferably sleeve-shaped adapter 5 is mounted on the proximal opening of the working channel/hose 3 facing the user, which forms a, if applicable, standardized connection point/interface 51 for medical devices. In the exemplary embodiment shown, this is a Luer cone for connecting syringes and the like. The sleeve-shaped adapter 5 also forms a stop 52 running circumferentially on its inner side for the axial fixation of the working channel/hose 3 with respect to the proximal adapter 5. Here, too, the inherent elasticity of the hose 3 can advantageously form an additional force-locking connection with the adapter 5.

The working channel device 1 is attached proximally with a proximal fixing means 6, preferably on the endoscope grip 23, in particular in such a way that the adapter 5 is approximately at the height of the inlet 24 of the regular working channel of the retrofitted endoscope 20. The fixing means 6 is manufactured integrally with the adapter 5 in the exemplary embodiments shown and described below, but can also be designed as a separate modular component.

A first configuration of the proximal fixing means 6 provides two wings/fixing lugs 61 which extend away from the outer circumference of the sleeve-shaped adapter 5 in order to be able to at least partially or completely encompass an endoscope grip 23 when mounted. On the side of the outer circumference of the adapter opposite the wings 61, a hook 62 is arranged which serves to fix a Velcro tape 64 (or another tension strap). This Velcro tape/tension strap 64 can then be fixed via the hook 62 and guided through eyelets 63 at the free ends of the wings 61 to fix/tie down the proximal fixing means 6 and thus the working channel device 1 to the grip 23.

A second configuration of the proximal fixing means 6 provides for two, in particular bow-shaped (convexly curved), cantilevers 65 at the free ends of the wings 61, which are configured to grip around an endoscope grip 23 in the manner of clasps or forceps (partially circularly). The wings 61 and/or the cantilevers 65 have a certain inherent elasticity so that the grip 23 can be snapped in between them. For the secure fixation of the cantilevers 65, oppositely (concavely) curved hooks 66 are provided at their free ends. With the help of these hooks 66, the free ends of the cantilevers 65 can be secured against spreading apart by means of a rubber ring, an O-ring or the like, whereby the proximal fixing means 6 is securely held on the grip 23 of the endoscope 20. In other words, the cantilevers 65, with the hooks 66 arranged at their free ends, essentially form an Ω shape, the feet of which are secured against an opening movement by an additional elastic band.

A third configuration of the working channel device 1 differs first in that the working channel device has an additional cover hose 7. Furthermore, the design of the distal fixing means (the distal cap) 4, the adapter 5 as well as the proximal fixing means 6 is slightly different from the first and the second configuration, as explained in more detail below.

Figure 11:
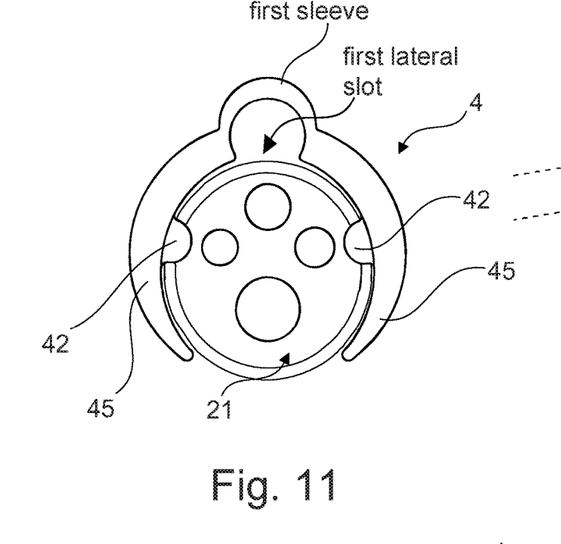
FIG. 11 shows a frontal view of a distal end cap mounted on an endoscope head according to a second configuration.
Figure 12:
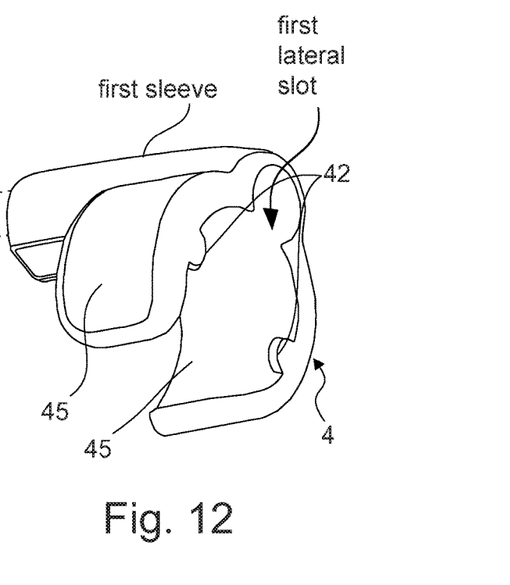
FIG. 12 shows a perspective view of the end cap according to the second configuration.
Figure 13:
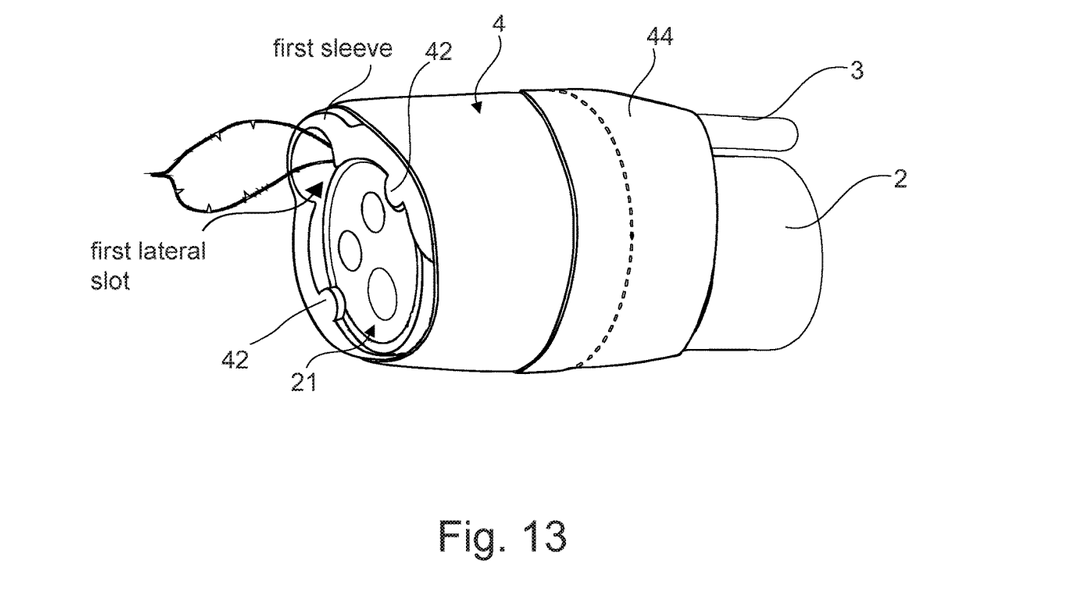
FIG. 13 shows a perspective view of the end cap mounted on an endoscope head according to the second configuration.

As FIGS. 11 to 13 show, the distal fixing means or respectively the distal cap 4 of the third configuration of the invention is provided with lug-like endoscope-head stops 42, which extend radially inwards from the crescent-shaped clamping arms 45 of the fixing portion 43 and form a stop with the front surface of the endoscope head 21, so that slipping of the distal cap 4 toward the proximal side is reliably prevented. In addition, the endoscope-head stops 42 facilitate a defined position of the distal outlet of the additional working channel 3 with respect to the endoscope head 21 when mounting the distal cap 4 on the endoscope head 21.

Figure 14:
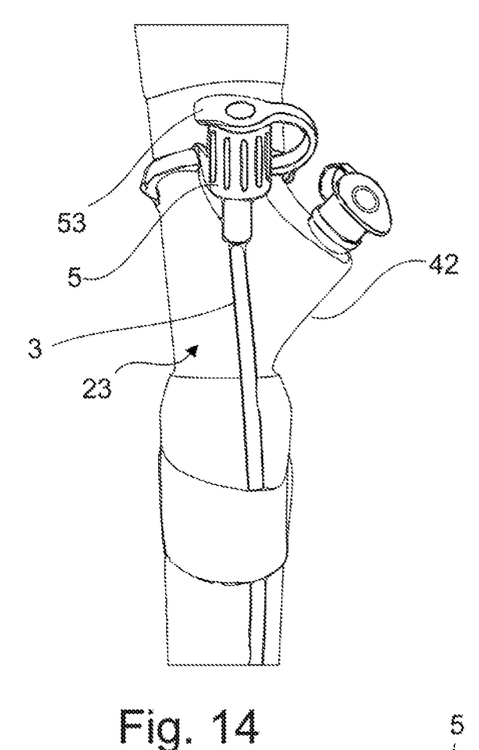
FIG. 14 shows a proximal fixing means of a working channel device according to a third configuration.

The adapter 5 of the working channel device 1 of the third configuration shown in FIG. 14 can be closed with an (integrally-manufactured) cap 53 on the one hand and on the other hand has a valve device in its interior which is not shown in further detail and which prevents unintentional intrusion of foreign bodies into the working channel 3 as well as unintentional leakage of body fluid and the like.

Figure 15:
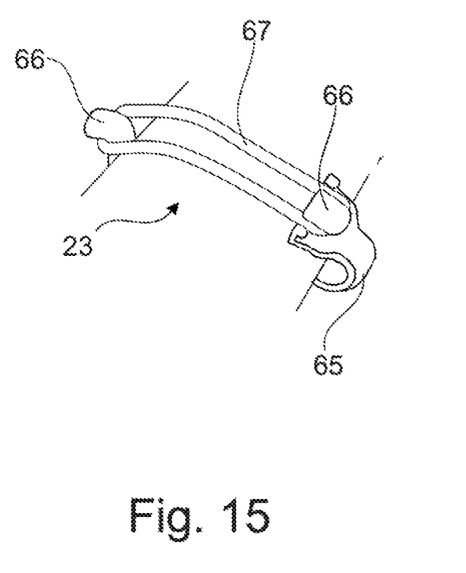
FIG. 15 shows a detail of an adapter arranged at the proximal fixing means with closure and valve.
Figure 16:
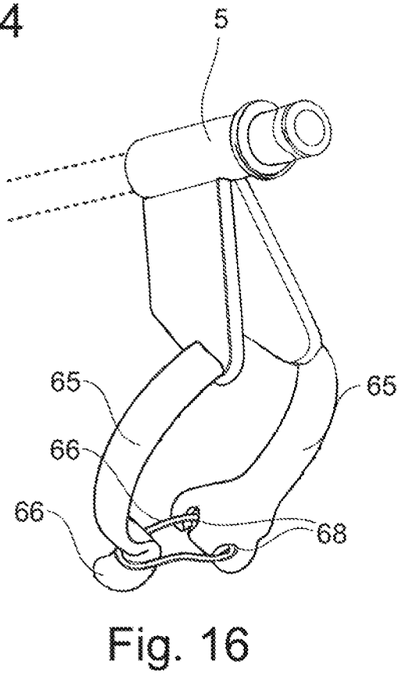
FIG. 16 shows a perspective view of the proximal fixing means according to the third configuration.

The proximal fixing means 6 of the third configuration shown in FIGS. 15 and 16 is similar to that of the second configuration in that it also comprises two crescent-shaped clasps 65 integrally formed with the adapter 5, which are configured to grip around an endoscope grip 23 and to be tightened against each other by means of a hook 66 formed on their distal end portions and a rubber ring 67. The proximal fixing means 6 of the third configuration of the invention has additional retaining slits or eyelets 68 which, adjacent to one of the hooks 66, are molded into the edge of the free end of the clasp 65 carrying the hook 66. The retaining slits 68 are narrower in the area of their opening and more bulbous on the inside, so that the rubber ring 67 can only be pushed/snapped through the narrow point under elastic deformation, but expands again in the bulbous area of the retaining slits 68. In this way, the rubber ring 67 is securely held at the proximal fixing means 6 and cannot slip from the hooks 66 and fall to the floor during assembly.

Figure 17:
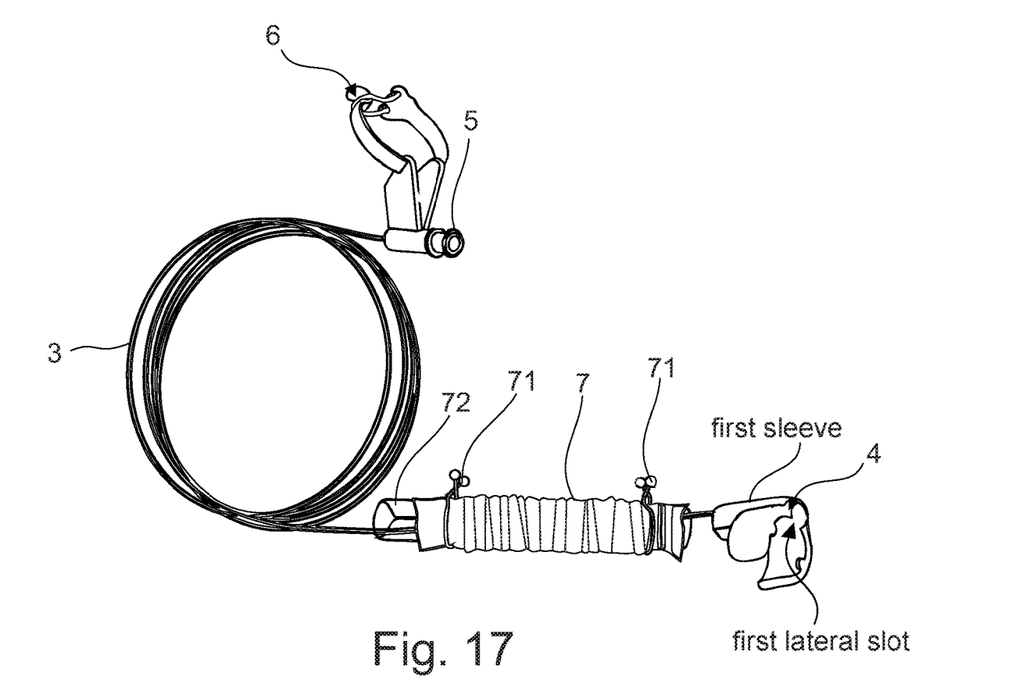
FIG. 17 shows a view of a complete working channel device according to a configuration without endoscope.
Figure 18:
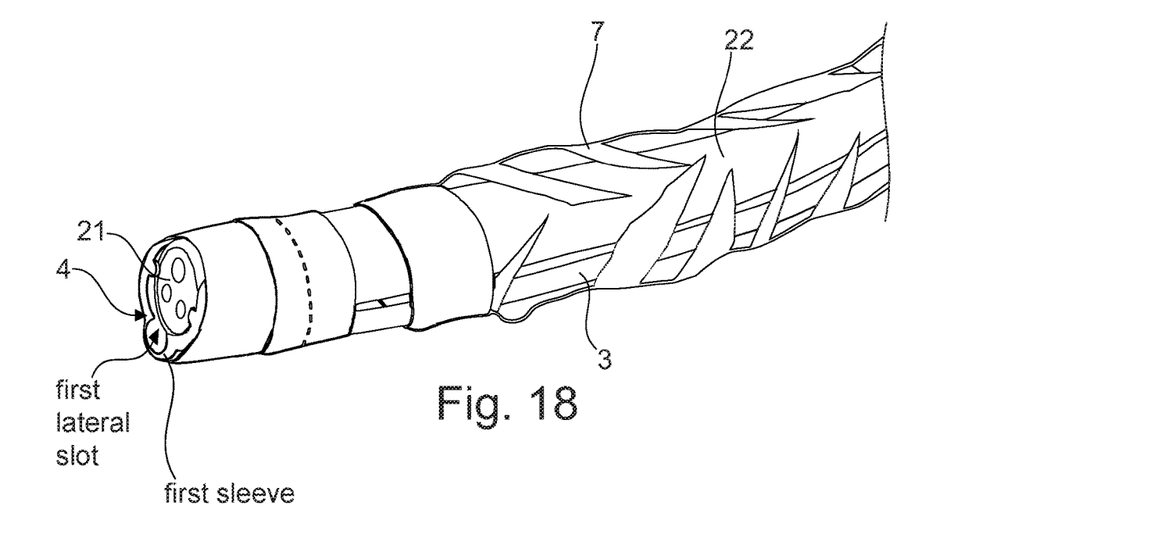
FIG. 18 shows a detail of a working channel device according to a configuration with cover hose.

The cover hose 7, which was added as an additional component in the third configuration, is best seen in FIGS. 17 and 18. As shown in FIG. 18, the cover hose 7 is attached proximally behind the endoscope head 21 and pulled towards the endoscope grip 23 over the endoscope shaft 22 of the adapted endoscope 2 and the additional working channel 3. As can be seen in FIG. 18, the additional working channel 3 can, under certain circumstances, protrude slightly from the endoscope shaft 22 when the endoscope shaft 22 is bent accordingly, so that a gap is formed. In such a case, the cover hose 7 prevents tissue from becoming trapped in said gap, which could lead to tissue trauma. The working channel device 1 shown in FIG. 17 includes cable twist clips 71 for temporary fixation of the cover hose 7 during mounting as well as a small (guiding) tube 72, which makes it easier to slide the gathered cover hose 7 onto an endoscope 2 to be adapted.

In the following, a typical mounting procedure of the working channel device 1 on an endoscope 2 is described using the third configuration described above.

At first, the endoscope is pushed through the small tube 72 of the cover hose 7 included with the working channel device 1.

Subsequently, the distal fixing means 4 is placed on the endoscope tip 21 so that the stops 42 contact the front side of the endoscope tip 21. The working channel 3, which is still relatively rotatable at this point, is positioned in the circumferential direction according to the desired application. The distal fixing means is then fixed to the endoscope using the adhesive strips 31 included in the set.

The AWC adapter 5 is attached to the endoscope grip 23 with the proximal fixing means 6 on the right or left (depending on preference) next to the endoscope working channel inlet by placing the cantilevers or clasps 65 around the grip above the working channel. The adapter 5 is then secured on the clasps 65 by attaching the rubber ring 67 to the provided hooks 66.

A further adhesive strip 31 on the endoscope shaft, approx. 10 cm below the AWC adapter 5, attaches it additionally to the endoscope grip 23.

The distal cable-twist clip 71 is removed, the hose end is attached to the endoscope 2 with an adhesive strip 31 at a distance from the adhesive strips 31 of the distal fixing means and the cover hose 7 (endoscope cover) is pulled back to the proximal end of the endoscope 2 using the small tube 72. It unrolls during this process. The cover hose 7 is smoothed towards the proximal end so that there is no excess material at the distal end. The remaining cable twist clip 71 and the small tube 72 are removed. To facilitate the introduction of the system, the surface of the cover hose 7 can be reduced by distributing the additional adhesive strips 31 over the cover hose 7 with distance to each other.

The invention claimed is:

1. A working channel device for mounting on an outer circumference of an endoscope with an endoscope grip and an endoscope head, the working channel device comprising:
    a tube-shaped or hose-shaped working channel,
    a distal fixing means, which is configured to grip around the endoscope, in a clamping or clasping manner,
    an adapter which comprises an adapter sleeve mounted on a proximal end region of the working channel of the working channel device and forming a connection point/interface for connecting medical devices,
    a proximal fixing means integrally connected to the adapter sleeve, the proximal fixing means comprising:
    a clamping or clasping device comprising two bracket arms which are elastically bendable away from each other to provide a clamping force to provide a connection to the endoscope grip in a clamping or clasping manner, with the first bracket arm and the second bracket arm respectively extending in a direction away from the adapter sleeve, and
    a spacer device integrally connecting the adapter sleeve and the clamping or clasping device to each other and holding the adapter sleeve and the clamping or clasping device at a distance with respect to each other, the spacer device comprising two lugs, each lug having a first end portion connected to the adapter sleeve and one of the two lugs having a second end portion connected to only one among the two bracket arms and another one of the two lugs having a second end portion connected to only the other one among the two bracket arms, such that each one of the two bracket arms of the clamping or clasping device is held at a distance from the adapter sleeve via one of the two lugs.

2. The working channel device according to claim 1 wherein the distal fixing means forms at least one endoscope-head stop which defines the distal fixing means in a form-fit manner in the axial direction with respect to the endoscope head.

3. The working channel device according to claim 2, wherein the endoscope-head stop is configured such that it abuts against a front side of an endoscope head of an endoscope adapted with the working channel device.

4. The working channel device according to claim 1, wherein the bracket arms, in particular in the region of free ends of the bracket arms, each form an eyelet for guiding a tape or strap.

5. The working channel device according to claim 4, further comprising a hook arranged on the side of the adapter remote from the bracket arms for guiding a tape or strap.

6. The working channel device according to claim 1, wherein the proximal fixing means comprises the two bracket arms which are two elastically bendable bow-shaped cantilevers, which curve to form a proximal accommodation between them in their relaxed non-bent position, the proximal accommodation being configured to accommodate the endoscope grip in a clamping manner between the bow-shaped cantilevers, by their elasticity.

7. The working channel device according to claim 6, wherein at least one of the bow-shaped cantilevers has a free end, a hook being formed at said free end, the hook being curved in an opposite direction to a direction of curvature of the cantilever, for holding a tape or strap, such that in the relaxed, non-bent position, the corresponding bow-shaped cantilever forming the hook forms one half of an omega-shape.

8. The working channel device according to claim 6, wherein at least one of the bow-shaped cantilevers has an edge area forming at least one retaining slit having a narrowed slit opening area in order to securely hold a tape or strap.

9. The working channel device according to claim 1, wherein the adapter has an integrated valve which prevents foreign bodies from entering the proximal end of the working channel and/or air or liquid from leaking from the proximal end of the working channel.

10. The working channel device according to claim 1, further comprising an additional cover hose adapted and configured to be pulled over the working channel and the endoscope adapted therewith.

11. The working channel device according to claim 1, wherein the adapter sleeve extends in a first direction, and the spacer device is connected to a circumferential side of the adapter sleeve and extends in a second direction which is different from the first direction.

12. The working channel device according to claim 1, wherein the two lugs have different respective extending directions than the respective two bracket arms.

13. The working channel device according to claim 1, wherein each of the two bracket arms is connected to a respective one of the two lugs at a respective connecting area, and in said connecting area, each bracket arm extends transversely with respect to the respective lug.

14. The working channel device according to claim 1, wherein the two lugs are non-connected to each other via their second end portions.

15. The working channel device according to claim 1, wherein the two lugs each have an intermediate portion extending away from the adapter sleeve and from each other.

16. A working channel device for mounting on an outer circumference of an endoscope with an endoscope grip and an endoscope head, the working channel device comprising:
   a tube-shaped or hose-shaped working channel,
   a distal fixing means, which is configured to grip around the endoscope, in a clamping or clasping manner,
   a proximal fixing means forming a clamping or clasping device, which is configured to provide a connection to the endoscope grip, in a clamping or clasping manner, and
   a sleeve-shaped adapter which is mounted or mountable on a proximal end region of the working channel of the working channel device, the adapter integrally forming the proximal fixing means and additionally forming a connection point/interface for connecting medical devices,
   the distal fixing means comprising:
   a first sleeve with a first accommodation with an at least partially circular cross-section accommodating the working channel, forming a through hole extending along an axial direction with respect to an axial direction of the endoscope head and laterally penetrating said first sleeve to form a first lateral slot, and
   a first crescent-shaped clamping arm extending from and being integrally formed with the first sleeve on a first side adjacent the first lateral slot and a second crescent-shaped clamping arm extending from and being integrally formed with the first sleeve on a second side adjacent the first lateral slot, the first clamping arm and the second clamping arm extending in a direction away from a longitudinal axis of the first sleeve and being curved to form a second accommodation between each other with an at least partially circular cross-section,
   the first accommodation and the second accommodation being connected via the first lateral slot, and a second slot being formed between a first free end of the first clamping arm and a second free end of the second clamping arm, and
   the first sleeve extending at an angle with a longitudinal axis of the first accommodation defined by the first sleeve and a longitudinal axis of the second accommodation defined by the first clamping arm and the second clamping arm approaching each other while extending distally, such that at a distal end face of the distal fixing means, a radially outer wall of the first sleeve and a radially outer wall of the first and second clamping arms essentially form a circular contour and at a proximal side of the first and second clamping arms, the first sleeve protrudes radially outwards from the radially outer wall of the first and second clamping arms.

17. The working channel device according to claim 16, wherein the clamping arms of the distal fixing means are crescent-shaped and together define a circular shape with their outer surfaces in a plane of a front surface of an adapted endoscope and the outer surface of the first sleeve defining the first accommodation protrudes beyond this circular shape in the radial direction by no more than half the diameter of the first accommodation.

18. The working channel device according to claim 16, wherein the first clamping arm and the second clamping arm each have a respective first radial thickness adjacent to the first lateral slot, and the first sleeve terminates at a distal first sleeve opening defined between the respective first radial thicknesses of the first clamping arm and the second clamping arm.

19. A working channel device for mounting on an outer circumference of an endoscope with an endoscope grip and an endoscope head, the working channel device comprising:
   a tube-shaped or hose-shaped working channel,
   a distal fixing means, which is configured to grip around the endoscope, in a clamping or clasping manner,
   a proximal fixing means forming a clamping or clasping device, which is configured to provide a connection to the endoscope grip, in a clamping or clasping manner, and
   a sleeve-shaped adapter which is mounted or mountable on a proximal end region of the working channel of the working channel device, the adapter integrally forming the proximal fixing means and additionally forming a connection point/interface for connecting medical devices,
   the distal fixing means comprising:
   a first sleeve with a first accommodation with an at least partially circular cross-section accommodating the working channel, which is accommodated in the first accommodation such that a distal end of the working channel is arranged proximally at a distance from a distal end of the first sleeve, and the first accommodation forming a through hole extending along an axial direction with respect to an axial direction of the endoscope head and laterally penetrating said first sleeve to form a first lateral slot opening at the distal end of the first sleeve extending proximally at least to the distal end of the working channel; and
   a first crescent-shaped clamping arm extending from and being formed integrally with the first sleeve on a first side adjacent the first lateral slot and a second crescent-shaped clamping arm extending from and being formed integrally with the first sleeve on a second side adjacent the first lateral slot, the first clamping arm and the second clamping arm extending in a direction away from a longitudinal axis of the first sleeve and being curved to form a second accommodation between each other with an at least partially circular cross-section, the first accommodation and the second accommodation being connected via the first lateral slot, and a second slot being formed between a first free end of the first clamping arm and a second free end of the second clamping arm,
   the first sleeve extending at an angle with a longitudinal axis of the first accommodation defined by the first sleeve and a longitudinal axis of the second accommodation defined by the first clamping arm and the second clamping arm approaching each other while extending distally, such that at least at a distal end of the first sleeve, instruments inserted through said first sleeve are deflectable radially inwards.

20. The working channel device according to claim 19, wherein a diameter of the first accommodation is smaller than a diameter of the second accommodation.

21. The working channel device according to claim 19, wherein a width of the first slot in a circumferential direction is more than half a diameter of the first accommodation.

22. The working channel device according to claim 19, wherein on an inner circumferential surface of the first sleeve, a projection is formed which contacts the distal end of the working channel to define a distal end position thereof.

23. An endoscope system comprising an endoscope with a flexible endoscope shaft, at the distal end of which an endoscope head is arranged and at the proximal end of which an endoscope grip is arranged, the endoscope system comprising a working channel device according to claim 1.

24. An endoscope system comprising an endoscope with a flexible endoscope shaft, at the distal end of which an endoscope head is arranged and at the proximal end of which an endoscope grip is arranged, the endoscope system comprising a working channel device according to claim 16.

25. An endoscope system comprising an endoscope with a flexible endoscope shaft, at the distal end of which an endoscope head is arranged and at the proximal end of which an endoscope grip is arranged, the endoscope system comprising a working channel device according to claim 19.

\* \* \* \* \*